United States Patent [19]

Endo

[11] Patent Number: 4,624,924
[45] Date of Patent: Nov. 25, 1986

[54] NOVEL COLLAGENASE "DISCOLYSIN" AND PRODUCTION METHOD THEREOF

[75] Inventor: Akira Endo, Tokyo, Japan

[73] Assignee: Kabushiki Kaisha Yakult Honsha, Tokyo, Japan

[21] Appl. No.: 708,637

[22] Filed: Mar. 6, 1985

[30] Foreign Application Priority Data

Mar. 9, 1984 [JP] Japan .................................. 59-45292

[51] Int. Cl.$^4$ .............................................. C12N 9/52
[52] U.S. Cl. .................................. 435/220; 435/253; 435/826; 530/825
[58] Field of Search ........................ 435/220, 253, 826; 260/112 R

[56] References Cited

U.S. PATENT DOCUMENTS

| 3,201,325 | 8/1965 | Barton | 435/220 |
| 3,677,900 | 7/1972 | Merkel | 435/220 |
| 3,684,658 | 8/1972 | Delin et al. | 435/220 X |
| 3,705,083 | 12/1972 | Chiulli et al. | 435/220 |
| 3,827,939 | 8/1974 | Tanaka et al. | 435/220 |
| 3,875,006 | 4/1975 | Belloc et al. | 435/220 |
| 3,923,600 | 12/1975 | Yoshimura et al. | 435/220 X |
| 4,268,434 | 5/1981 | Higerd et al. | 435/826 X |
| 4,315,988 | 2/1982 | Miwa et al. | 435/253 X |
| 4,404,194 | 9/1983 | Arala-Chaves | 260/112 R |

Primary Examiner—Howard E. Schain
Attorney, Agent, or Firm—Oblon, Fisher, Spivak, McClelland & Maier

[57] ABSTRACT

Disclosed herein is a novel collagenase "discolysin". It is useful for biochemical researches and the treatment of many diseases caused by collagen, such as hernia of intervertebral disc. It can be produced by culturing a discolysin-producing bacterium belonging to genus of Streptomyces in a culture medium and then collecting discolysin from the culture medium.

4 Claims, 2 Drawing Figures

NOVEL COLLAGENASE "DISCOLYSIN" AND PRODUCTION METHOD THEREOF

This invention relates to a novel collagenase "discolysin" having an activity capable of dissolving insoluble collagens and a production method thereof.

As a collagenase having an activity of dissolving insoluble collagens, the enzyme produced by *Clostridium histolycum* has been known most popularly. The collagenase from this bacterium has found wide-spread commercial utility as a laboratory reagent for various biochemical researches. Recently, it has also become possible to use it for the treatment of diseases such as low back pain and hernia of intervertebral disc since it can decompose the intervertebral disc collagen. However, this bacterium is an anaerobic pathogen known as a gas gangrene for many years and produces toxins. Accordingly, this bacterium is not suitable for the mass production of a collagenase because it is difficult to culture it in a large quantity as it is an anaerobic bacterium and in addition, it produces dangerous toxins. Thus, the present inventor has widely looked for a collagenase which has excellent characteristics, permits ready mass production and hence is economical, and can be produced by a bacterium. As a result, a novel collagenase has been found from a culture medium of a bacterium in the genus of Streptomyces, leading to completion of this invention.

Namely, this invention provides a novel collagenase which is useful for biochemical researches and the treatment of many diseases caused by collagen, such as hernia of intervertebral disc, and can be produced by a microorganism.

The above enzyme has been found to dissolve both non-denatured and denatured collagens. This enzyme will hereinafter be called "discolysin".

In one aspect of this invention, there is thus provided a novel collagenase "discolysin" having the following physical and chemical properties:

(1) Molecular weight: 60,000–70,000, (SDS-Gel electrophoresis); 90,000–110,000 (SDS-Gel electrophoresis; presence of 10 mM EDTA);
(2) Formation of two collagenase-active bands by the disc gel electrophoresis;
(3) Isoelectric point: pH 4.8 and 4.9 (determined by the focal electrophoresis);
(4) Elementary analysis data: C, about 43%; H, about 7%; N, about 13%;
(5) U.V. spectrum: FIG. 1;
(6) I.R. spectrum: FIG. 2;
(7) Precipitated by 45–81% saturation with ammonium sulfate;
(8) Adsorbed on an ion exchanger, DEAE cellulose;
(9) Decomposition of insoluble collagens and denatured collagen but extremely inert to casein;
(10) Optimum pH for decomposition of insoluble collagens: 7.6–8.0; and
(11) Inhibited by EDTA.

This invention relates also to a method for culturing a bacterium in the family of Actinomycetes and collecting discolysin from the cultured mixture, especially, for culturing a bacterium in the genus of Streptomyces and collecting discolysin from the cultured mixture.

In another aspect of this invention, there is also provided a method for producing a novel collagenase "discolysin", which comprises culturing a discolysin-producing bacterium belonging to genus of Streptomyces in a culture medium and then collecting discolysin from the culture medium.

The above and other objects, features and advantages of this invention will become apparent from the following description and appended claims, taken in conjunction with the accompanying drawings, in which:

Figure 1:
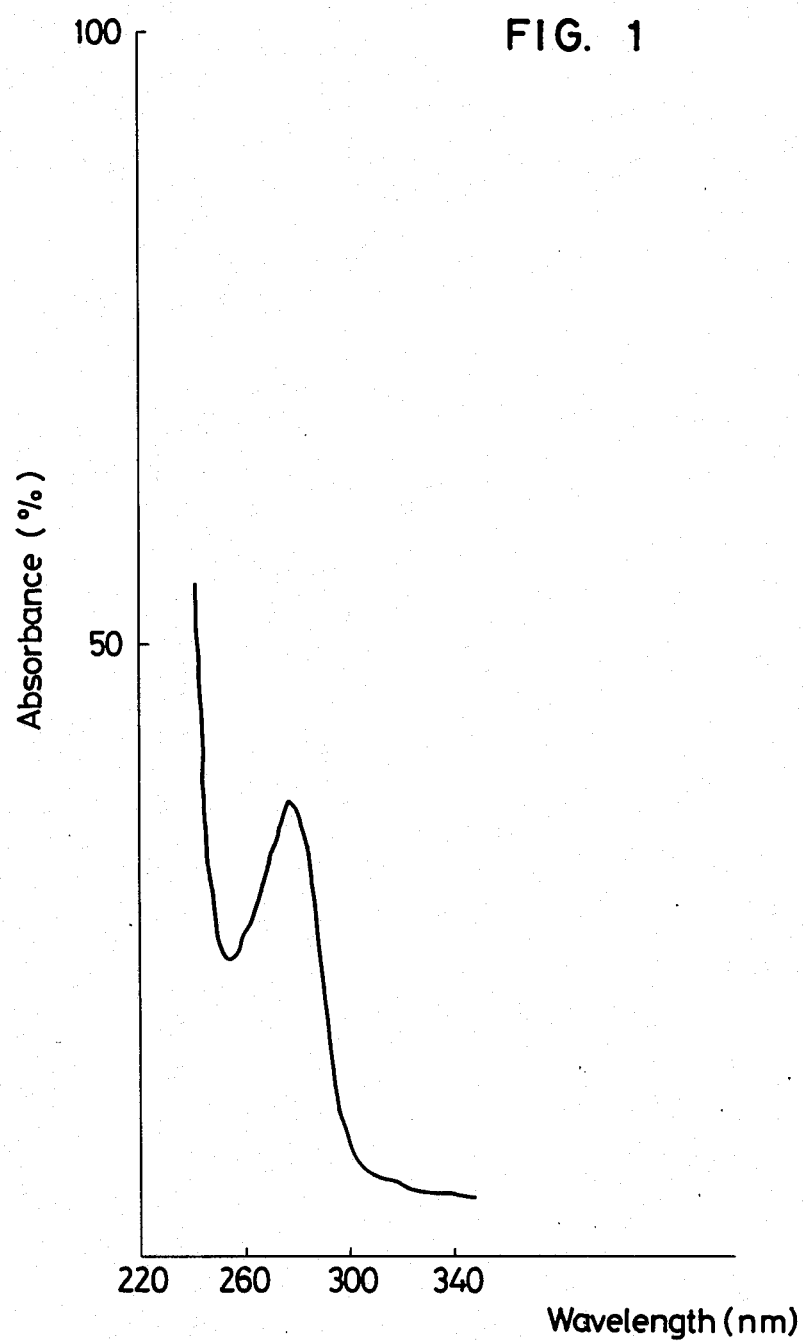
FIG. 1 is an ultraviolet absorption spectrum of discolysin.

Microorganisms useful in the practice of this invention are discolysin-producing bacteria in the genus of Streptomyces. As an exemplary strain which has been recognized to be particularly effective for the present invention, may be mentioned Streptomyces sp. C-51 strain. This strain has been deposited under FRI deposition FERM BP-710 with the Fermentation Research Institute, Agency of Industrial Science and Technology, Ministry of International Trade and Industry.

The above strain was isolated by the present inventor from soil which had been obtained at Ohira, Numazu. Its mycological characteristics are as follows:

(1) Form:

No fragmentation of its vegetative mycelia is observed. Its hyphae and spore chains have wavy to spiral structures and contain 20 or more spores therein. Namely, it has properties between the Retinaculum-Apertum (RA) type and the Spira type. A scanning electron microscopic observation has found that its spores are pillow-like and 0.6 - 0.8 x 1.0 -1.2 m$\mu$ large and its spore surfaces are smooth. Organs such as asci, sclerotia or zoospores are not observed.

(2) Characteristics of cell wall:

Its cell wall contains LL-diaminopimelic acid (LL-DAP) and glycine. No characteristic features are found on the saccharide which makes up the bacterium body.

(3) State of growth:

The state of its growth on various agar culture media were as shown in Table 1.

TABLE 1

| Culture medium | Growth | Color of back surface | Hyphae | Soluble pigment |
|---|---|---|---|---|
| Tryptone-yeast agar culture medium | Good. Light yellowish brown (10YR8/3) | Dull yellow orange (5YR7/2) | Abundant. Dull yellow orange (5YR7/2) | — |
| Yeast-malt agar culture medium | Good. Light yellowish brown (2.5Y6/3) | Dark yellowish brown (2.5Y4/2) | Abundant. Dark yellowish brown (5YR4/1) | — |
| Oat meal agar culture medium | Good. Bright olive gray (5Y7/1) | Bright brownish gray (5Y6/1) | Abundant. Grayish olive (5Y7/1) | — |
| Starch-inorganic salt agar culture medium | Good. Light yellowish brown (5Y7/1) | Yellowish brown (2.5Y6/2) | Abundant. Bright brownish gray (1Y6/2) | — |

TABLE 1-continued

| Culture medium | Growth | Color of back surface | Hyphae | Soluble pigment |
|---|---|---|---|---|
| Glycerin-asparagine agar culture medium | Good. Light yellow (2.5Y7/3) | Light yellow (2.5Y7/2) | Abundant. Bright brownish gray (10YR5/1) | — |
| Peptone-yeast-iron agar culture medium | Good. Yellowish white (2.5Y9/2) | Light yellowish brown (2.5Y8/4) | Abundant. Yellowish gray (5YR8/1) | — |
| Tyrosine agar culture medium | Good. Light yellowish brown (2.5Y5/1) | Yellowish brown (2.5Y5/3) | Abundant. Dark yellowish brown (5Y5/1) | — |
| Glycerin-calcium maleate agar culture medium | Good. Yellowish white (10YR7/2) | Dull yellow orange (10YR6/1) | Abundant. Grayish yellow brown (10YR5/1) | — |
| Nutrient agar culture medium | Good. Light yellowish brown (2.5Y7/3) | Yellowish brown (2.5Y6/2) | Abundant. Bright brownish gray (10YR6/1) | — |
| Sucrose-nitrate agar culture medium | Weak. Colorless (N-9) | Bright brownish gray (10YR6/1) | Medium. Light brownish gray (10YR7/1) | — |
| Glucose-nitrate agar culture medium | Weak. Colorless (N-9) | Bright brownish gray (10YR6/1) | Medium. Light brownish gray (10YR7/1) | — |
| Glucose-asparagine agar culture medium | Weak. Colorless (N-9) | Light brownish gray (10YR7/1) | Abundant. Bright brownish gray (10YR6/1) | — |

(4) Physiological properties:

Its growth temperature ranged from 10 to 40° C. with the optimum growth temperature being near 28° C. The starch-decomposing capacity, peptonizing capacity and coagulating capacity of skim milk, and liquefying capacity of gelatin (on a glucose-peptone gelatin culture medium) were all positive. On the other hand, the producing capacity of a melanine-like pigment, nitric acid reducing capacity, hydrogen sulfide producing capacity and cellulose-decomposing capacity were not observed.

(5) Anabolism of carbon sources:

It metabolized D-glucose, L-arabinose, D-mannit and D-fructose very well. It metabolized D-xylose and inositol rather well. However, it did not metabolize or metabolized extremely little L-rhamnose, raffinose, sucrose and cellulose.

Summarizing the above properties, it can be concluded that the above strain is in the genus of Streptomyces, is of the RA or RAS type of the Gray series, has smooth spore surfaces, and is of the melanine-negative (non-chromogenic) type.

Needless to say, bacteria in the genus of Streptomyces which bacteria are other than the above-mentioned bacterium may also be used including their varieties and variant strains, so long as they show discolysin-producing capacity.

Discolysin can be produced in a culture medium by culturing a discolysin-producing strain aerobically in accordance with any culturing method which is known as a culturing method for Actinomycetes. Discolysin-producing bacteria grow at 10°-40° C. A temperature range of 25°-35° C. is generally preferred for the production of discolysin. For culturing a discolysin-producing bacterium in the genus of Streptomyces, it is possible to use any nutrient source known for culturing Actinomycetes and other microorganisms. For example, glucose, starch, dextrin, glycerin, sucrose and the like may be used as carbon sources. Of these carbon sources, glucose and sucrose are carbon sources both suitable for the production of discolysin.

Nitrogen sources known for the growth of Actinomycetes and other microorganisms can all be used for the production of discolysin. For example, peptone, meat extract, yeast, yeast extract, soybean powder, peanut powder, corn steep liquor, rice bran, gelatin, various fish meal, inorganic nitrogen, etc. may be used.

When discolysin is produced by culturing a discolysin-producing bacterium, one or more inorganic salts and metal salts may be added if necessary. One or more heavy metals may also be added in trace amounts.

Discolysin can be obtained by culturing a discolysin-producing bacterium aerobically. For this purpose, a routinely-employed aerobic culturing method, for example, the solid culturing method, shake culturing method or aerated-stirring culturing method may be employed. If defoaming is required during culturing or in the course of sterilization of a culture medium, a defoaming agent such as silicone oil, surfactant or the like may be used. The preferred culturing temperature may be within the range of 25°-35° C.

The activity of discolysin can be measured by the following method in which discolysin dissolves collagen. Namely, 5 ml of a 0.067 M phosphate buffer (pH 7.4; containing 0.45% of NaCl), 1 ml of a discolysin solution and 25 mg of collagen obtained from calf Achilles tendons are reacted at 37° C. for 18 hours (For a control, no enzyme is added). After the reaction, the liquid reaction mixture is filtered and 2.0 ml of the ninhydrin reagent is added to 0.2 ml of the filtrate. The resultant mixture is heated for 20 minutes in boiling water. Thereafter, the mixture is cooled in running water. The volume of the resultant mixture is adjusted to 10 ml with water. Fifteen minutes later, its absorbance is measured at a wavelength of 600 nm. From a standard curve obtained using L-leucine as a reference, the amount of amino acids freed during the reaction is determined. From the thus-determined amount, the physiological activities of discolysin can be determined.

The culturing is continued until discolysin accumulates substantially. The extraction and separation of this substance from the cultured mixture may be carried out by suitably combining various methods on the ground of its properties found out by the present inventor, as will be shown in Examples which will be given hereinafter. Namely, there are the salting-out method making use of ammonium sulfate or the like, the precipitation relying upon an organic solvent such as acetone or methanol, the chromatography employing various ion exchangers, the gel filtration making use of various carriers, a variety of electrophoreses, the ultrafiltration, the lyophilization method, the dialysis method, the chromatofocusing, and so on. Discolysin can be isolated from the cultured mixture by combining these methods or using them repeatedly.

Physical and chemical properties and biological activities of discolysin will next be given.

Figure 2:
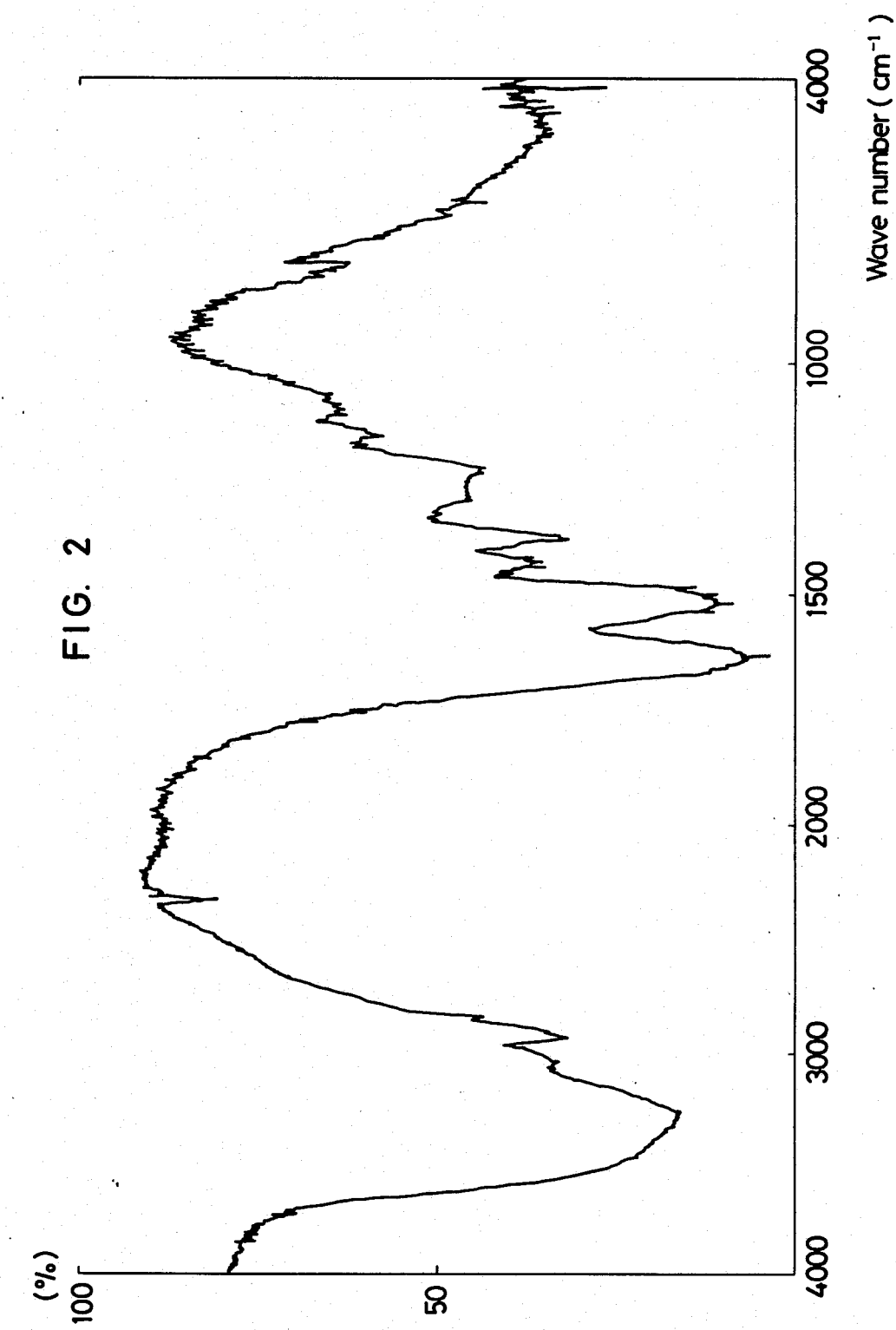
FIG. 2 is an infrared absorption spectrum of discolysin.

(1) Molecular weight: 60,000–70,000 (determined by the SDS polyacrylic amide electrophoresis); 90,000–110,000 (determined by the SDS polyacrylic amide electrophoresis; presence of 10 mM EDTA);
(2) Formation of two collagenase-active bands by the disc gel electrophoresis;
(3) Isoelectric point: pH 4.8 and 4.9 (determined by the focal electrophoresis);
(4) Elementary analysis data: C, about 43%; H, about 7%; N, about 13%;
(5) U.V. spectrum: FIG. 1;
(6) I.R. spectrum: FIG. 2;
(7) Precipitated by 45–81% saturation with ammonium sulfate;
(8) Adsorbed on an ion exchanger, DEAE cellulose;
(9) Decomposition of insoluble collagens and denatured collagen but extremely inert to casein;
(10) Optimum pH for decomposition of insoluble collagens: 7.6–8.0;
(11) Activity-inhibited by EDTA.
(12) Its decomposition activity for insoluble collagens is either equal to or slightly higher than the collagenase produced by Clostridium histolycum; and
(13) Its acute toxicity ($LD_{50}$): 1 g/Kg or more (determined by its oral administration to mice).

Discolysin can be used widely in a variety of biochemical, physiological and pharmacological researches which require decomposition of collagens. In addition, it can also be used extensively for the prevention and treatment of various diseases caused by collagens, for examples, hernia of intervertebral disc, Peyronie disease (spongiositis), certain liver diseases, etc. For example, a dog under narcosis was subjected to abdominal incision. While confirming an intervertebral disc by palpation, a discolysin solution (0.05 ml) was administered by injection through back peritoneum to nucleus pulposus located in a central part of the intervertebral disc. One week after the administration, the dog was killed and the intervertebral disc was observed. As a result, the nucleus pulposus was found to have been significantly dissolved where 100 units (ABC units) or more of discolysin was administered per each intervertebral disc. By the way, no serious toxicity or side effect was observed.

As mentioned above, it has been confirmed that discolysin is effective for diseases caused by certain disorder in collagens and can hence be used as medical drugs, non-medical drugs or food additives.

Discolysin may be administered either orally or non-orally, for examples, in the form of capsules, tablets, injectable preparations or the like. Its dose may vary depending on age, symptom, body weight, etc. However, 1–100 mg/day may usually be administered in 1–3 portions to an adult. It may however be administered in a larger dose or more often as needed.

Examples of this invention will hereinafter be described. Since various properties of discolysin have been found as mentioned above by the present invention, it is however possible to make various modifications to the collection of discolysin from a cultured mixture or its related substances on the basis of these findings. The present invention is thus not necessarily limited to the following Examples but should include all methods readily inferable from findings and knowledge which have already been reported. Example 1:

Fifteen liters of a culture medium containing 1% of sucrose, 1% of peptone, 0.3% of gelatin, 0.2% of yeast extract, 0.2% of $Na_2HPO_4$, 0.25% of $Na_2CO_3$ and 0.04% of $MgSO_4\ 7H_2O$ were charged in a jar having an internal volume of 30 liters. After sterilization, Streptomyces C-51 strain was inoculated and cultured aerobically at 30° C. for 30 hours. After completion of the culturing, a filtrate (12 liters) was obtained. Ammonium sulfate was then added to the filtrate. Fractions which precipitated at 45–80% saturation were collected. They were dissolved and dialyzed against 10 mM tris-HCl buffer (pH 7.5)/4 mM $CaCl_2$, followed by adsorption on a DEAE cellulose column (3.2×26 cm). The column was then developed with a gradient system which consisted of 1 liter of the above buffer and 1 liter of a solution obtained by adding 1 mole of NaCl to the same buffer, thereby collecting discolysin fractions. These fractions were then dialyzed against 10 mM citric acid (Na) buffer (pH 7.0)/4 mM $CaCl_2$, followed by adsorption on a DEAE cellulose column (2.0×26 cm) maintained under the same buffer conditions. Thereafter, the column was developed with a gradient system which consisted of 1 liter of the above buffer and 1 liter of 10 mM citric acid (Na) buffer (pH 4.0)/4 mM $CaCl_2$, thereby collecting principal active fractions. These fractions were then dialyzed against 0.2 mM $CaCl_2$ and lyophilized to obtain 51 mg (as proteins) of purified discolysin.

I claim:

1. A collagenase "discolysin" having the following physical and chemical properties and produced by culturing a bacterium belonging to the genus of Streptomyces in a culture medium and then collecting discolysin from the culture medium:
(1) Molecular weight: 60,000–70,000 (SDS-Gel electrophoresis); 90,000–110,000 (SDS-Gel electrophoresis; presence of 10 mM EDTA);
(2) Formation of two collagenase-active bands by disc gel electrophoresis;
(3) Isoelectric point: pH 4.8 and 4.9 (determined by focal electrophoresis);
(4) Elemental analysis data: C, about 43%; H, about 7%; N, about 13%;
(5) U.V. spectrum: FIG. 1;
(6) I.R. spectrum: FIG. 2;
(7) Precipitated by 45–81% saturation with ammonium sulfate;
(8) Adsorbed on an ion exchanger, DEAE cellulose;
(9) Decomposes insoluble collagens and denatured collagen but is extremely inert to casein;
(10) Optimum pH for decomposition of insoluble collagens: 7.6–8.0; and
(11) Inhibited by EDTA.

2. A method for producing a novel collagenase "discolysin", as recited in claim 1, which comprises culturing a discolysin-producing bacterium belonging to the genus of Streptomyces in a culture medium and then collecting discolysin from the culture medium.

3. A method according to claim 2, wherein the discolysin-producing bacterium is Streptomyces C-51 strain.

4. The method of claim 2, wherein said culturing is conducted aerobically in a culture medium at 25°–35° C.

* * * * *